United States Patent [19]

Fellows et al.

[11] Patent Number: 5,140,136
[45] Date of Patent: Aug. 18, 1992

[54] HEAT TREATMENT DISINFECTING OR STERILIZING DEVICE AND METHOD

[75] Inventors: Adrian N. Fellows; Godfrey P. Mountain, both of Burnley, United Kingdom

[73] Assignee: Fibre Treatment (Holdings) Limited, Lancashire, England

[21] Appl. No.: 623,976
[22] PCT Filed: Jun. 20, 1989
[86] PCT No.: PCT/GB89/00686
  § 371 Date: Feb. 22, 1991
  § 102(e) Date: Feb. 22, 1991
[87] PCT Pub. No.: WO89/12468
  PCT Pub. Date: Dec. 28, 1989

[30] Foreign Application Priority Data
Jun. 24, 1988 [GB] United Kingdom ............... 88115104

[51] Int. Cl.$^5$ ........................................ H05B 3/34
[52] U.S. Cl. .................................. 219/521; 219/386
[58] Field of Search ............ 219/521, 385, 386, 524, 219/525, 545, 529

[56] References Cited

U.S. PATENT DOCUMENTS

| | | | |
|---|---|---|---|
| 2,485,140 | 10/1949 | Cordero | 219/524 |
| 2,581,212 | 1/1952 | Spooner | 219/529 |
| 3,648,019 | 3/1972 | Brewitz | 219/386 |
| 4,163,896 | 8/1979 | McAvinn | 219/525 |
| 4,533,821 | 8/1985 | Sato | 219/545 |

FOREIGN PATENT DOCUMENTS 1194591  6/1970  United Kingdom ............... 219/529

Primary Examiner—Teresa J. Walberg
Attorney, Agent, or Firm—Mason, Fenwick & Lawrence

[57] ABSTRACT

A container is provided having a hinged lid; a heating element in the container includes a fabric having resistance wires woven into it. The fabric has selvedges, each containing a conductor to which the resistance wires are connected in parallel. The heating element is flexibly deformable and is stretched by tensioning elements. An article placed on the heating element is urged into intimate contact with it by a resiliently deformable pad.

17 Claims, 4 Drawing Sheets

HEAT TREATMENT DISINFECTING OR STERILIZING DEVICE AND METHOD

DESCRIPTION

1. Technical Field

The invention relates to a method and device for the disinfection or sterilisation of articles by heat.

Many different articles which may become biologically contaminated require disinfection or sterilisation so that they are decontaminated and rendered safe for their intended purpose. Often this disinfection or sterilisation is accomplished by various chemical means, but it is generally recognised that where possible the efficient application of heat is the most appropriate means of achieving the desired end of sterilisation or disinfection.

2. Background Art

Relatively elevated temperatures are required to achieve adequate disinfection and even higher temperatures are required for sterilisation. A major problem is ensuring the requisite temperature is attained throughout the heating device and its load. Various pieces of equipment have been used to achieve this end, notably hot-air ovens, autoclaves, steamers, pressure cookers etc. Other forms of radiation have also been utilised for disinfection and sterilisation, for instance gamma rays or ultra violet rays. To be effective such devices are expensive and complicated.

DISCLOSURE OF INVENTION

According to the invention there is provided a heat treatment disinfecting or sterilising device characterised by comprising a container defining a void for receiving an article to be disinfected or sterilised, an electrical resistance heating element arranged in the void, the heating element being flexibly deformable and being adapted for close contact with the article to be disinfected or sterilised and comprising a textile fabric containing electrical resistance members in the form of wires connected in parallel by means of conductors in both selvedges, the wires being woven into the fabric, tensioning means for stretching or maintaining the heating element in a dimensionally stable initial condition, and a resiliently deformable pad in the void by which the article to be disinfected or sterilised and the heating element are pressed into contact.

Preferably the wires are spirally wound on cores of fibres constituting the textile fabric. The fabric may be composed of glass fibres or of fibres of an aramid.

The heating element may be arranged along at least one side of the void, and a movable member may provide access to the void. Preferably the heating element covers substantially the whole of the said one side of the void. The container may be arranged to be portable and may be formed with hinged lid for providing access to the void. Preferably the container is lined with a thermally insulating material. Preferably the resiliently deformable pad is compressible. The resiliently deformable pad may be filled with a thermally insulating material. The heating element may be adapted to envelop the article to be heat treated, e.g. the element may be foldable about the article. If desired, the heating element may be provided with a thin electrically insulating outer layer of a heat resisting material. The tensioning means may be such that the heating element is held in a substantially flat initial condition.

Preferably, the heating element is resiliently as well as flexibly deformable; preferably the resiliently deformable pad substantially fills the void.

From another aspect the invention is a method of heat treating an article comprising bringing the article into close contact with a heating element of a heat treatment device as described above, and passing an electrical current through the heating element for a given length of time, and wherein the article and the heating element are pressed into contact to deform resiliently the heating element into close contact with the article and are held in close contact during the heat treatment.

The article and the heating element may be held in contact for a time sufficient to achieve sterilisation of the article. The article may be heated to a temperature in the range 160° to 250° C.

In this invention the conductive wires are connected in parallel as this permits instruments and other conductive articles to be in direct contact with the conductive heating wires while minimising the risk of causing electrical short circuits. With the requirement to shield the conductive wires removed or reduced, overall heat capacity, weight and size can be minimised hence greatly contributing to the efficiency of the invention both electrically and thermally. Also, at the power inputs required in this invention this parallel wiring ensures the electrical safety of the device. It will then not be shorted out, nor will electric shocks be received by persons touching the element, even while wearing jewellery or with wet hands. Also it will be possible to load wet instruments. The low heat capacity required of the heating element will also contribute significantly to making this invention safe to use. In some circumstances it may however, as indicated above, be considered desirable to provide the heating element with a thin electrically insulating outer layer of a heat resisting material such, for example, as a woven aramid cloth, to prevent the possibility of the heating wires being electrically bridged and thus to some extent short circuited by the articles to be heat treated.

The heating element is housed desirably within a container having good thermal insulating properties and in such a manner as to permit items to be disinfected or sterilised to be laid on, covered over, wrapped in, or otherwise contacted with or brought into close juxtaposition with the heating fabric. The fact that the articles to be treated can be placed in direct or very close contact with the resistance wires of the heating fabric can greatly improve the efficiency of heat transfer and help minimise the wasteful heating of components of the equipment itself. The heating fabric may be connected via its conductive selvedge or via suitably constructed bus-bars in the apparatus itself, to a suitable power source, e.g. the electric mains or a suitable battery or solar cell. However, such may be the efficiency of the invention in heating articles to be disinfected or sterilised, that only a very modest electrical supply may be required so in the case of a mains supply the heating fabric may be connected via a transformer, variable resistance, thyristor, or a similar device capable of moderating the supply.

A device as described in outline above has a number of novel and unique advantages over previously available means of sterilising or disinfecting articles reliably by heat.

In the first instance, a device in accordance with the invention is capable of precise control and very uniform application of heat and may be constructed relatively inexpensively. Further it is capable of relatively quickly attaining a usefully high temperature with a very low power input. For instance utilising a polyester heating fabric approximately 30×30 cm having a total resistance for the whole cloth of 12 ohms, a temperature of 121° C. may be obtained in under 4.5 minutes for an input of 36 volts, in a suitable insulated system. Further, as the heat capacity of said heating fabric is very low, and close contact is possible between the element and contents, giving excellent heat transfer and, hence the total amount of heat energy required is optimised, it is possible for such a suitable insulated system to be of relatively simple, lightweight, compact and inexpensive construction. For example in one embodiment, the heating fabric may be located and tensioned by means of springs attached to the conductive selvedge of the fabric and to the inside of a suitable case, for instance a moulded polypropylene carrying case. Below the heating fabric in the case base is a layer of fibre-glass batting with an aluminised Melinex (RTM) face. In the lid of the case is further insulation in part in the form of a deformable cushion having an insulating filling, for instance of glass fibre and having a scrim reinforced aluminised Melinex exterior. On the cushion surface which faces the heating fabric are constructed locating lugs, loops or pockets for items of equipment. Hence when the lid is closed the items to be heat treated are brought into contact with the heating fabric and are surrounded by the deformable, reflecting and insulating cushion, hence heat transfer to the load is maximised and the air space is minimised. Air is a very poor heat transfer medium.

In such an example it is possible to heat the fabric up to say 120° C. very quickly, yet in a matter of seconds after discontinuation of supply to the heating fabric it is of a temperature which is safe to touch. Further, at useful low voltages, the properties of such a heating fabric when the resistance wires are in parallel are such that it is possible to have it in direct contact with the items to be sterilised eve if these items are conductive or wet. Therefore for a given required attainment temperature for an item the total heat energy necessary to be supplied is minimised. Further, said heating element is very light and flexible.

More particularly therefore, there may be provided by the invention a heat treatment disinfecting or sterilising device comprising a heating fabric substantially as described in U.K. Patent 2,110,909, said heating fabric being capable of heating to a temperature of at least 120° C., this temperature to be attained in a short time, for instance less than 5 minutes, when the applied voltage is less than 50 V. The said heating fabric should desirably be capable of sustaining this temperature in a suitably insulated enclosure for a time which is of value in the disinfection of items contaminated with bacteria, viruses, fungi, bacterial spores, or other life forms.

The construction of the container for the heating element is also important insofar as, if not adequately thermally insulated, then the heating fabric will either not attain sufficiently high temperature for a low applied voltage or will be impractically slow in attaining the requisite temperature. Also, if the container parts in juxtaposition to the heating fabric have a significant heat absorbing capacity, then they will impede the attainment of adequate temperature is a usefully short time. Useful insulating materials in this context are fibre-glass, mineral wool, and various forms of ceramic insulation materials. These may be utilised alone or as composites with each other; or in combination with reflective materials, e.g. in aluminised form; or in combination with insulating polymer films, coatings, strips or sheets particularly useful in this respect are polyester films, though other polymers may be of value for example nylon, Nomex (RTM), Tyvek (RTM), acrylics, polycarbonate, ABS, PVC, PVF, PVDC etc.

An example of disinfecting apparatus according to the present invention would comprise a container, box or receptacle having a lid capable of being opened and closed by means of a hinge, slide or other form of separation and fixing. This container would be suitably insulated by reflective polyester faced insulating material and aluminised glass cloth. The size of the lumen or void may usefully be reduced to a minimum in equipment covered by this invention, by judicious selection of flexible or deformable insulation components. Between these insulating components would be a heating fabric of stainless steel wound polyester weft fibre connected in parallel to copper strand selvedges acting as bus-bars. Such a heating device is shown in the accompanying drawings.

In one embodiment of the invention, this heating fabric would be approximately 30 cm by 30 cm having 19 bands of 12 resistance wires of 1 ohm resistance. Therefore, as these bands of resistance wires are arranged in parallel then the total resistance of the heating fabric equals 1/R band + 1/R band + 1/R band etc. = 1/R Total Therefore 19/228 = 1/R Total . . . R = 228/19 = 12 ohms In the above described insulated container, the application of an applied voltage of 36 volts raises the temperature of said element and its immediate surroundings, including an appropriate load of items to be sterilised or disinfected to a temperature of 120° C. in around four and a half minutes. It will readily be apparent by calculation that as:

$$OHMS = VOLTS^2/WATTS: 12 = 36^2/W \text{ therefore } W = 108$$

then this rapid and effective heating is obtained for a power input of only 108 watts, or a watt density of 1200 watts/m².

This heating time may be approximately halved by the addition of a second similar heating cloth, or the use of a cloth of twice the length folded over, for example, as a pocket or pouch. This is a very efficient utilisation of energy compared to alternative thermal disinfecting or sterilising devices.

Further, that as, Watts = volts × amps then for the single cloth example:

$$108 = 36 \times Amps \text{ therefore } Amps = 108/36 \text{ therefore } Amps = 3.$$

then such a power requirement may readily be supplied from the mains via a compact transformer which may be an integral part of the apparatus or which may be a separate power pack to be simply plugged in the apparatus.

Obviously a piece of equipment as exemplified above would require appropriate electrical circuitry, controls, and operating aids, such as on-off switch, thermostat, operational indicator lights or display timers etc. The design of such is well known to those skilled in that art.

It is further appropriate to insulate the bus-bars either by glass-tape or similar or by design of the enclosure or insulation such that instruments or other items being disinfected do not contact the bus-bars and potentially cause short-circuits.

It is of functional benefit to the user of equipment as exemplified above to be able to remove and use items which have been sterilised or disinfected immediately their treatment is finished. It has been noted, that an advantage of this invention is that the heating fabric may cool down extremely rapidly, while the contents being treated will cool down less rapidly. It is therefore proposed to provide means of more rapid cooling if so desired, either by means of blowing filtered air across the load, or by providing a water bag, sachet or flow cell preferably flexible in nature which can be contacted with the load on completion of its treatment cycle. Such a cooling device may be integral to the equipment or separate therefrom.

A further example of a device according to this invention would be similar to the above but would utilise a heating fabric constructed of glass fibres so as to permit operating temperatures of up to 400° C., but preferably of between 150° C. and 220° C. Such temperatures quickly achieve sterilisation, using dry heat. For such equipment involving heating fabrics operating at watt densities of 3 kw/m$^2$ and higher, obviously, different power supply transformers and more sophisticated circuitry, controls and operating aids would be required. Such items and design are readily accomplished by those skilled in the art.

Certain items to be sterilised may be sensitive to such high temperatures as those above, therefore it is proposed in a further embodiment of the invention to have a device or apparatus broadly as exemplified above, but also comprising a means of introducing to the items to be sterilised a chemical possessing suitable antimicrobial activity. Such a chemical would be chosen from amongst those known as disinfectants, but more particularly from amongst those known to have activity against bacterial spores, for example, a dialdehyde such as glutaraldehyde or succinaldehyde, an aldehyde such as formaldehyde; chlorine, chlorine releasing agents; chlorine dioxide; iodine or iodine releasing agents or compositions; ethylene oxide; or one of the other chemicals which has from time to time been proposed as a sporicidal agent. The said antimicrobial may be introduced as a spray, liquid, aerosol, vapour, gas or other appropriate phase, under such control and mechanism as to quantity, contact time etc., as is known to be appropriate for the particular agent. Such information is known to those skilled in the relevant art.

A typical cycle for such a piece of equipment might involve heating to 70° C., introducing a pulse spray of 2% aqueous glutaraldehyde for 2 minutes while the temperature climbs to 105° C. at which temperature the $GA+H_2O$ would become gases and could be purged during a holding time at say 121° C.

It will be appreciated that a device which is the subject of this invention could be used to heat treat articles which had received a pre-soak in a cold sterilising solution. The electrical safety of the invention would permit the direct loading of wet instruments.

BRIEF DESCRIPTION OF DRAWINGS

There follows a description, by way of example, of embodiments of the invention, reference being made to the accompanying schematic drawings, in which.

BEST MODES FOR CARRYING OUT THE INVENTION

Figure 1:
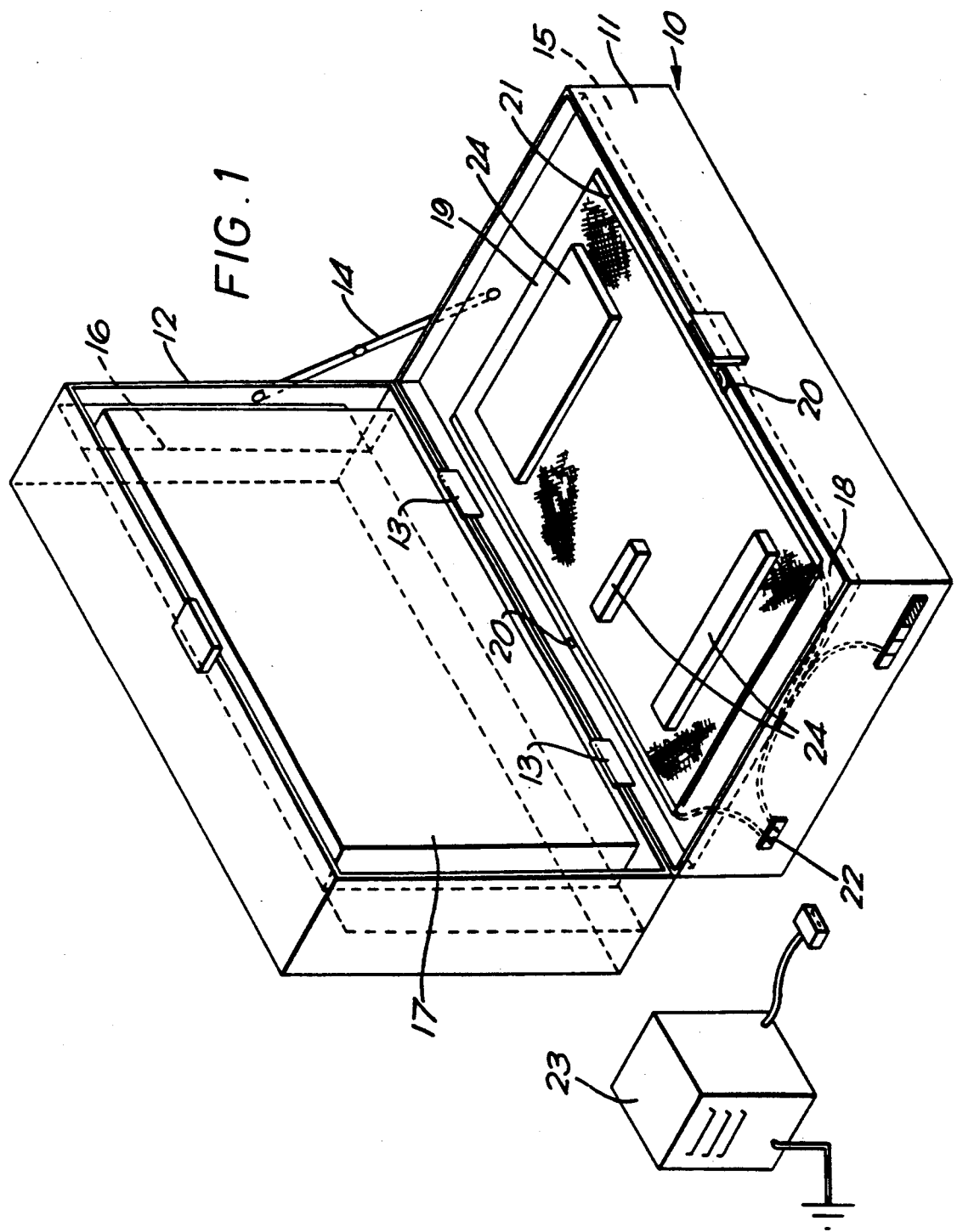
FIG. 1 is an isometric view of one embodiment of a heat treatment disinfecting and sterilising device in accordance with the invention.

FIG. 1 shows a heat treatment disinfecting or sterilising device comprising a case 10 having a base 11 and a lid 12 hinged to the base by hinges 13. An articulated strut 14 is provided to hold the lid in a raised position but allow it to be lowered on to the base to close the case. The void within the case contains layers 15 and 16 of fibreglass batting disposed respectively in the base and the lid and faced with aluminised Melinex and is substantially filled by an insulation pillow 17 disposed in the lid and comprising glass fibres enclosed in aluminised Melinex. Any spaces between the layer 15 and the sides of the base 11 are filled with a composite bulk fill insulation 18 faced with aluminised glass fibre matt. On top of the layer 15 is provided a sheet 19 of heating fabric as hereinbefore described, the sheet 19 having supports 20 attached to its selvedges to stretching the sheet flat. Only two supports 20 are shown in FIG. 1 but more will usually be provided to ensure uniform tension. Bus-bars 21 of copper and insulated in glass cloth are provided along the selvedges of the sheet 19, the resistance wires in the sheet being connected in parallel by the bus-bars which are themselves connected through an electrical connector 22 on the case to a transformer unit 23. In use, the lid of the case is opened, items 24 to be sterilised are placed on the sheet 19 and the lid is closed so that the articles are pressed closely against sheet 19 by the insulation pillow. Electric current is supplied for a predetermined period to cause sterilisation before removal of the items 24.

Figure 2:
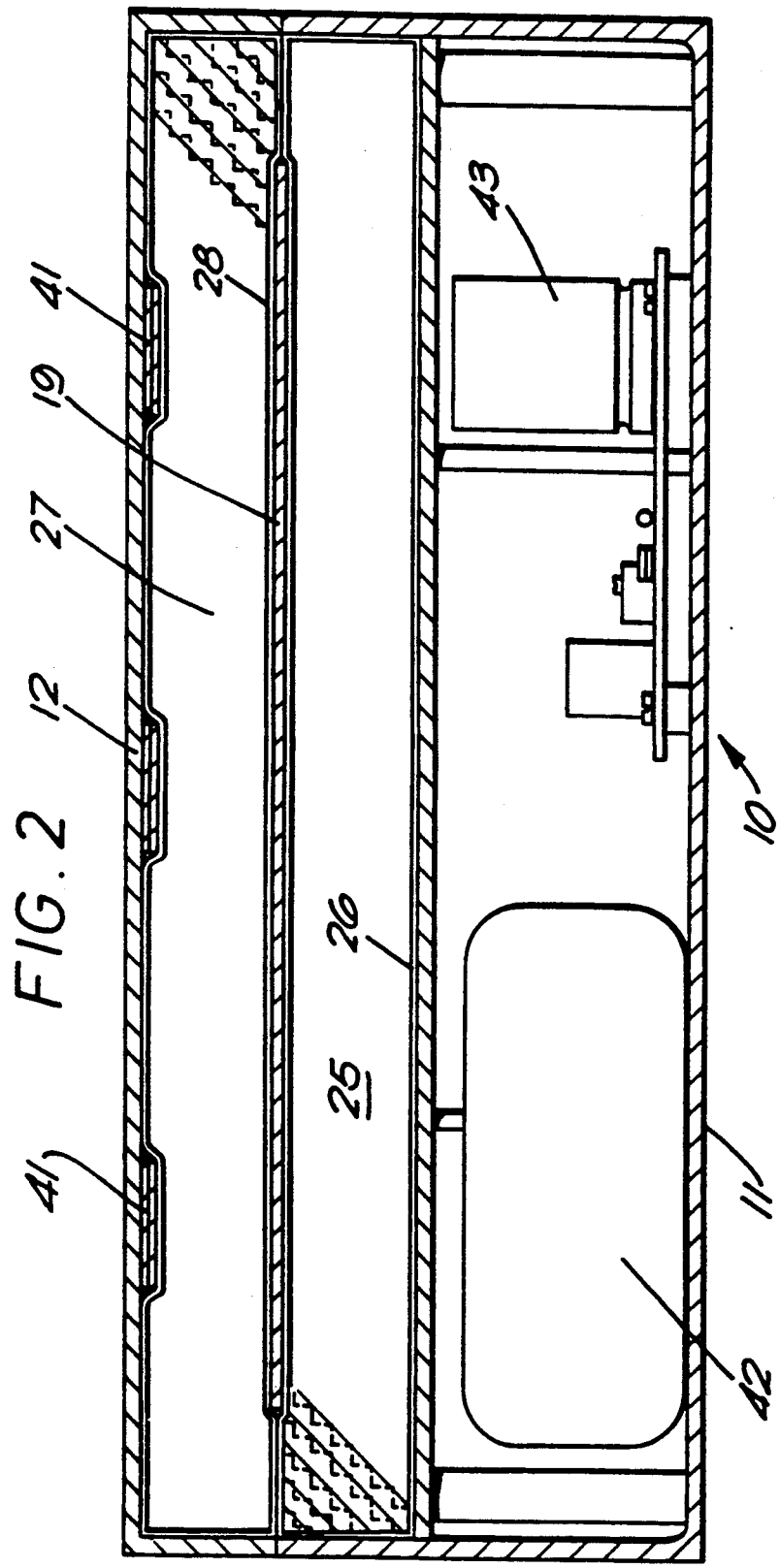
FIG. 2 is a cross-sectional view of another embodiment.

The embodiment of FIG. 2 is in many respects similar to that of FIG. 1 and where appropriate the same reference numerals are used. However, in this embodiment, a thermal cushion 25 of rockwool in a glass cloth cover 26 is provided in the base 11 below the heating element 19 and a thermal cushion 27 of rockwool in a glass cloth cover 28 is provided in the lid 12 to press items to be sterilised against the heating element, these cushions constituting a resiliently deformable pad substantially filling the space in the case. The cushion 27 may be held in the lid 12 by self-adhesive strips 41 which adhere to the cushion and lid. The base 11 may contain, in a bottom cavity, control instruments including, for example, a transformer 42 and a printed circuit board 43.

Figure 3:
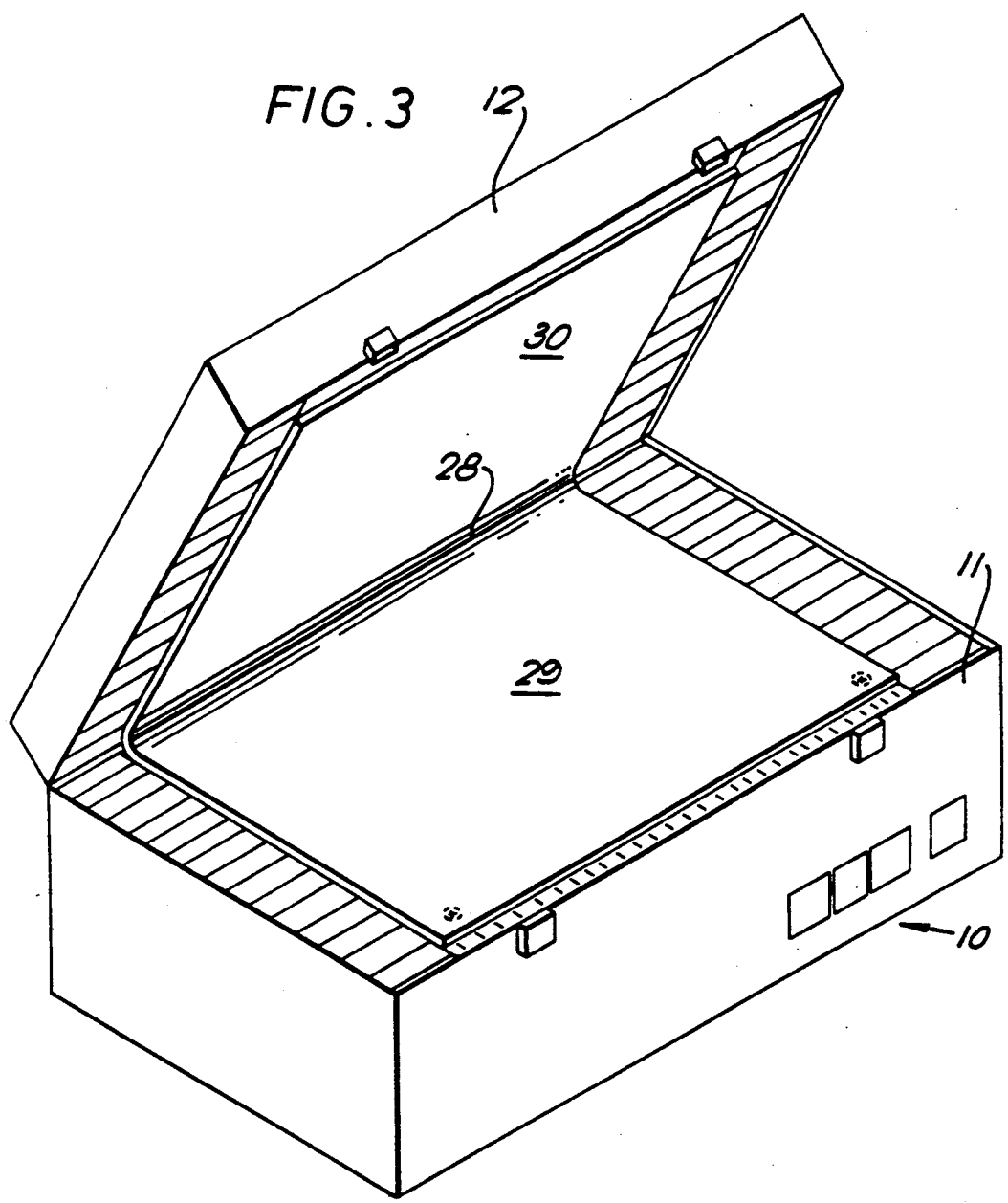
FIG. 3 is an isometric view of a further embodiment.

The embodiment of FIG. 3 is also similar in many respects to the embodiments of FIGS. 1 and 2 but instead of employing a sheet of heating fabric 19 only in the base 11, it employs a single sheet folded at 28 into two parts 29 and 30 which are secured respectively to the base and lid. Thus, when items to be sterilised are inserted and the lid is closed, the folded sheet completely surrounds the items.

Figure 4:
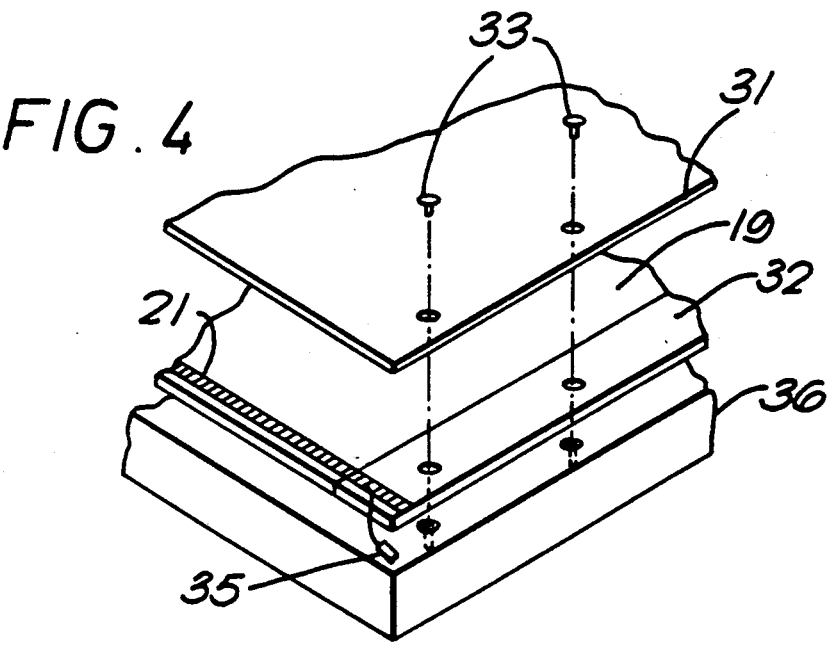
FIGS. 4, 5 and 6 show details of the embodiment of FIG. 3, which may also be used in the other embodiments.
Figure 5:
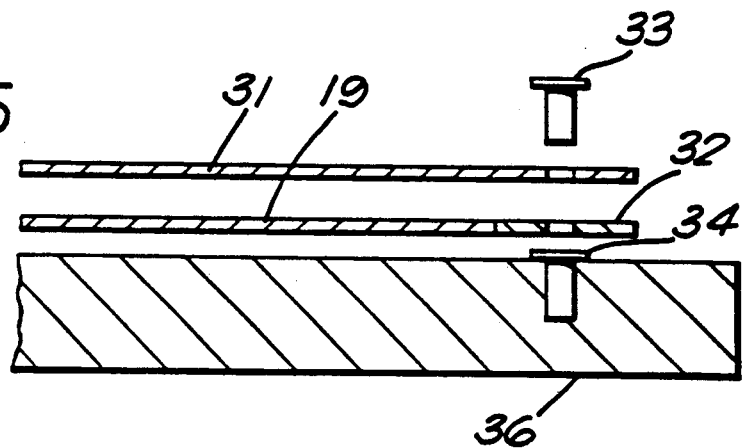
Figure 6:
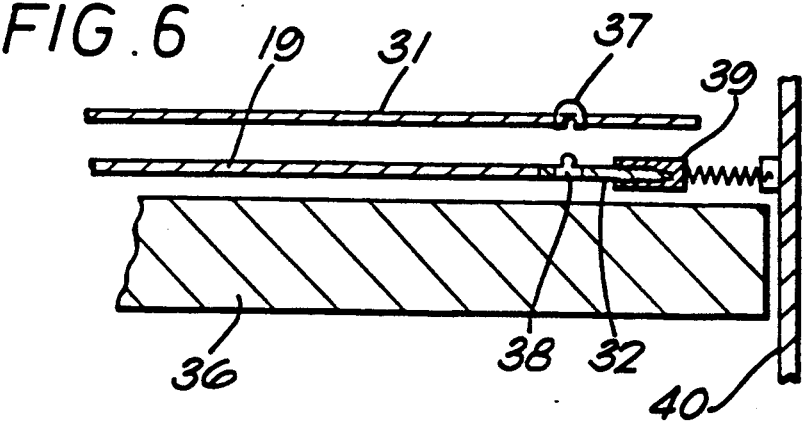

FIGS. 4 and 5 show a preferred arrangement applicable to all three of the embodiments of FIGS. 1 to 3, in which the sheet 19 is covered by a sheet 31 of electrically insulating, heat-resistant and heating-conducting material (e.g. Nomex). The sheet 31 therefore makes contact with the items to be sterilised. Quick-release, push fit electrical connectors 35 may be provided to the bus-bars 21. The sheet 19 has edges 32 of woven material which do not contain resistance wires and which are for securing purposes. The sheets 19 and 31 may be connected in face-to-face contact by pins or clips 33 which pass through holes in the sheet 31 and the edges 32 of the sheet 19 and engage in sockets 34 in backing insulation blocks 36 (which may be formed as previously described) to support and tension the sheets 19 and 31. In an alternative arrangement, shown in FIG. 6, support and tensioning of the sheets is provided by press-stud fastenings 37, 38 between the sheet 31 and the edges 32 of the sheet 19 and by clamps 39 which are crimp fixed to the edges 32 and spring-urged towards a wall 40 of the case 10.

INDUSTRIAL APPLICABILITY

The device and method of the invention are therefore useful with many articles which require disinfecting or sterilising.

We claim:

1. A heat treatment disinfecting or sterilizing device comprising:
    a container defining a void for receiving an article to be disinfected or sterilized,
    an electrical resistance heating element in the void, the heating element being flexibly deformable and comprising a textile fabric having selvedges with conductors therein, electrical resistance wires woven into the fabric, and connected in parallel to the conductors in both selvedges, said heating element comprising a first part and a second part overlying said first part, said first and second parts being foldably connected, whereby to envelope an article to be disinfected or sterilized between said first and second parts,
    tensioning means for stretching the heating element in a dimensionally stable initial condition, and
    means for urging a said article placed on said heating element into close contact with said heating element.

2. The heat treatment disinfecting or sterilizing device according to claim 1, wherein said wires are spirally wound on cores of fibers of the textile fabric.

3. The heat treatment disinfecting or sterilizing device according to claim 1, wherein said fabric is composed of glass fibers.

4. The heat treatment disinfecting or sterilizing device according to claim 1, wherein said fabric is composed of fibers of an aramid.

5. The heat treatment disinfecting or sterilizing device according to claim 1, wherein said heating element is positioned along at least one side of the void, and said container comprises a movable member which provides access to the void.

6. The heat treatment disinfecting or sterilizing device according to claim 5, wherein said heating element covers substantially one side of the void.

7. The heat treatment disinfecting or sterilizing device according to claim 1, wherein said container comprises a hinged lid for providing access to the void.

8. The heat treatment disinfecting or sterilizing device according to claim 1, said container being lined with a thermally insulating material.

9. The heat treatment disinfecting or sterilizing device according to claim 1, wherein said means for urging said article comprises a resiliently deformable compressible pad.

10. The heat treatment disinfecting or sterilizing device according to claim 9, wherein said resiliently deformable pad is filled with a thermally insulating material.

11. The heat treatment disinfecting or sterilizing device according to claim 1, wherein said heating element is provided with a thin electrically insulating and heat transmitting outer layer.

12. The heat treatment disinfecting or sterilizing device according to claim 1, wherein said tensioning means comprises means for holding said heating element substantially flat when there is no article on it.

13. The heat treatment disinfecting or sterilizing device according to claim 1, wherein said heating element is resiliently deformable.

14. The heat treatment disinfecting or sterilizing device according to claim 1, wherein said means for urging comprises a resiliently deformable pad substantially filling the void.

15. A method of disinfecting or sterilizing an article by heat treatment comprising the steps of:
    bringing the article into close contact with a heating element of a heat treatment disinfecting or sterilizing device comprising a textile fabric having electrical resistance wires woven thereinto and connected in parallel to conductors in the selvedges of the fabric,
    passing an electrical current through said heating element for a given length of time, and
    pressing and holding the article and said heating element into contact to resiliently deform said heating element into close contact with the article during the heat treatment.

16. The method according to claim 15, further comprising the step of:
    holding the article and said heating element in contact for a time sufficient to achieve sterilization of the article.

17. The method according to claim 15, further comprising the step of:
    heating the article to a temperature in the range of 160° to 250° C.

* * * * *

UNITED STATES PATENT AND TRADEMARK OFFICE
CERTIFICATE OF CORRECTION

PATENT NO. : 5,140,136

DATED : August 18, 1992

INVENTOR(S) : Adrian N. Fellows, Godfrey P. Mountain

It is certified that error appears in the above-identified patent and that said Letters Patent is hereby corrected as shown below:

On the title page, Item [73]:

Change "Treatment" to -- Treatments --

Signed and Sealed this

Twenty-sixth Day of October, 1993

*Attest:*

BRUCE LEHMAN

*Attesting Officer*     *Commissioner of Patents and Trademarks*